US010328083B1

(12) United States Patent
Decker et al.

(10) Patent No.: US 10,328,083 B1
(45) Date of Patent: Jun. 25, 2019

(54) COMPOSITIONS AND METHODS FOR TREATING STROKE

(71) Applicants: David Andrew Decker, Tampa, FL (US); Keith Pennypacker, Wesley Chapel, FL (US)

(72) Inventors: David Andrew Decker, Tampa, FL (US); Keith Pennypacker, Wesley Chapel, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 15/147,958

(22) Filed: May 6, 2016

Related U.S. Application Data

(62) Division of application No. 14/433,172, filed as application No. PCT/US2013/065380 on Oct. 17, 2013, now abandoned.

(60) Provisional application No. 61/715,443, filed on Oct. 18, 2012.

(51) Int. Cl.
*A61K 31/55* (2006.01)
*A61K 38/48* (2006.01)

(52) U.S. Cl.
CPC ............ *A61K 31/55* (2013.01); *A61K 38/482* (2013.01); *C12Y 304/21068* (2013.01)

(58) Field of Classification Search
None
See application file for complete search history.

(56) References Cited

U.S. PATENT DOCUMENTS

| 5,723,606 A | 3/1998 | Tanaka et al. |
| 5,827,832 A * | 10/1998 | Sandage, Jr. ...... A61K 31/7068 424/94.64 |
| 6,503,915 B2 * | 1/2003 | Grotta .................. A61K 31/52 514/15.1 |
| 6,645,959 B1 | 11/2003 | Bakker-Arkema et al. |
| 6,740,648 B2 | 5/2004 | Ghazzi et al. |
| 6,761,895 B2 | 7/2004 | Sawada et al. |
| 7,192,951 B2 | 3/2007 | Bakker-Arkema et al. |
| 7,687,494 B2 | 3/2010 | Patel et al. |
| 8,101,782 B2 | 1/2012 | Rupniak et al. |
| 8,372,830 B2 * | 2/2013 | Liu ........................ A61K 31/55 514/212.01 |
| 2003/0103983 A1 | 6/2003 | Pressler |
| 2008/0107641 A1 | 5/2008 | Kuebler |
| 2008/0221084 A1 | 9/2008 | Liu et al. |
| 2008/0275093 A1 | 11/2008 | Garvey et al. |
| 2008/0306044 A1 | 12/2008 | Costanzo et al. |
| 2010/0311642 A1 | 12/2010 | J-m.Riviere et al. |
| 2011/0105621 A1 * | 5/2011 | Poulsen ............... A61K 31/137 514/654 |
| 2012/0122820 A1 | 5/2012 | Diedrichs et al. |
| 2015/0238502 A1 | 8/2015 | Decker et al. |

OTHER PUBLICATIONS

Reagan-Shaw et al. "Dose Translation from Animal to Human Studies Revisited". FASEB J. Mar. 2008; 22(3):659-661.*
Hacke et al. "Association of Outcome with Early Stroke Treatment: Pooled Analysis of ATLANTIS, ECASS, and NINDS rt-PA Stroke Trials". Lancet, 2004; 363:768-774.*
Yuan J. "Neuroprotective Strategies Targeting Apoptotic and Necrotic Cell Death for Stroke". Apoptosis. 2009; 14:469-477. (Year: 2009).*
International Search Report and Written Opinion for PCT/US2013/065380 dated Jan. 28, 2014.
Lemmens-Gruber, et al., "Vasopressin Antagonists", Cellular and Molecular Life Sciences, vol. 63, 2006, pp. 1766-1779.
Udelson, et al., "Acute Hemodynamic Effects of Conivaptan, a Dual V1A and V2 Vasopressin Receptor Antagonist, in Patients with Advanced Heart Failure", Circulation, Journal of the American Heart Association, 2001; 104: 2417-2423.

* cited by examiner

*Primary Examiner* — Leslie A. Royds Draper
(74) *Attorney, Agent, or Firm* — Thomas|Horstemeyer, LLP

(57) ABSTRACT

Provided herein is a method of treating a subject believed to have suffered a stroke. This method comprises administering to the subject a therapeutically effective amount of a composition comprising conivaptan or an active derivative, stereoisomer, pro-drug, or pharmaceutically acceptable salt thereof.

13 Claims, 4 Drawing Sheets

| 6 hr Treatment Start | | | | | | | |
|---|---|---|---|---|---|---|---|
| | Surgery Day | | Post-op day 1 | | | | Post-op day 2 | |
| Treatments | 6 hr post | 9 hr post | 8 am | 12 pm | 4 pm | 8 pm | 8 am | 12 pm |
| NS | 1.4ml saline (0.9%) | | 1.4ml saline (0.9%) | | | | 1.4ml saline (0.9%) | Euth. |
| 5%IM | 2.4ml 5% infused 10" | 1.4ml 5% saline | 1.4ml 5% saline | | | | 1.4ml 5% saline | Euth. |
| C | Bolus Conivaptan 0.5 ml | 0.1 ml Conivaptan | 0.1 ml Conivaptan | | | | 1.4ml saline (0.9%) | Euth. |
| C5%M | Bolus Conivaptan 0.5 ml | 0.1 ml Conivaptan + 1.4ml 5% saline | 0.1 ml Conivaptan + 1.4ml 5% saline | | | | 1.4ml 5% saline | Euth. |
| C5%IM | 2.4ml 5% infused 10" + Bolus Conivaptan 0.5 ml | 0.1 ml Conivaptan + 1.4ml 5% saline | 0.1 ml Conivaptan + 1.4ml 5% saline | | | | 1.4ml 5% saline | Euth. |
| 24 hr Treatment Start | | | | | | | | |
| | Surgery Day | | Post-op day 1 | | | | Post-op day 2 | |
| Treatments | 6 hr post | 9 hr post | 8 am | 12 pm | 4 pm | 8 pm | 8 am | 12 pm |
| NS | 1.4ml saline (0.9%) | | 1.4ml saline (0.9%) | | | | 1.4ml saline (0.9%) | Euth. |
| 5%IM | 1.4ml saline (0.9%) | | 2.4ml 5% infused 10" | 1.4ml 5% saline | | | 1.4ml 5% saline | Euth. |
| C | 1.4ml saline (0.9%) | | Bolus Conivaptan 0.5 ml | 0.1 ml Conivaptan | | | 0.1 ml Conivaptan | Euth. |
| C5%M | 1.4ml saline (0.9%) | | Bolus Conivaptan 0.5 ml | 0.1 ml Conivaptan + 1.4ml 5% saline | | | 0.1 ml Conivaptan + 1.4ml 5% saline | Euth. |
| C5%IM | 1.4ml saline (0.9%) | | 2.4ml 5% infused 10" + Bolus Conivaptan 0.5 ml | 0.1 ml Conivaptan + 1.4ml 5% saline | | | 0.1 ml Conivaptan + 1.4ml 5% saline | Euth. |

FIG. 1

COMPOSITIONS AND METHODS FOR TREATING STROKE

CROSS REFERENCE TO RELATED APPLICATIONS

This application is a divisional of co-pending U.S. patent application Ser. No. 14/433,172, filed on Apr. 2, 2015, entitled "COMPOSITIONS AND METHODS FOR TREATING STROKE," the contents of which is incorporated by reference herein in its entirety.

U.S. patent application Ser. No. 14/433,172, filed on Apr. 2, 2015, entitled "COMPOSITIONS AND METHODS FOR TREATING STROKE," is the U.S. National Stage Entry of now expired Patent Cooperation Treaty Application No.: PCT/US2013/065380, filed on Oct. 17, 2013, entitled "COMPOSITIONS AND METHODS FOR TREATING STROKE," the contents of which is incorporated by reference herein in its entirety.

Patent Cooperation Treaty Application No.: PCT/US2013/065380, filed on Oct. 17, 2013, entitled "COMPOSITIONS AND METHODS FOR TREATING STROKE," claims the benefit of and priority to U.S. Provisional Patent Application No. 61/715,443, filed on Oct. 18, 2012, entitled "COMPOSITIONS AND METHODS FOR TREATING STROKE," the contents of which is incorporated by reference herein in its entirety.

BACKGROUND

Stroke is a general term for acute brain damage resulting from disease of blood vessels. This presents a serious problem to society, with about 500,000 people dying from or becoming permanently disabled by stroke in the United States each year. Stroke can be classified into two main categories: hemorrhagic stroke (resulting from leakage of blood outside of the normal blood vessels) and ischemic stroke (cerebral ischemia due to lack of blood supply).

The three main mechanisms of ischemic stroke are thrombosis, embolism and systemic hypoperfusion (with resultant ischemia and hypoxia). In each of these types of stroke, the area of the brain that dies as a result of the lack of blood supply thereto is called an infarct. Obstruction of a cerebral artery resulting from a thrombus which has built up on the wall of a brain artery is generally called cerebral thrombosis. In cerebral embolism, the occlusive material blocking the cerebral artery arises downstream in the circulation (e.g. an embolus is carried to the cerebral artery from the heart). Because it is difficult to discern whether a stroke is caused by thrombosis or embolism, the term thromboembolism is used to cover both these types of stroke. Systemic hyperfusion may arise as a consequence of decreased blood levels, reduced hematocrit, low blood pressure, or inability of the heart to pump blood adequately.

When symptoms of stroke last less than 24 hours and the patient recovers completely, the patient is said to have undergone a transient ischemic attack (TIA). The symptoms of TIA are a temporary impairment of speech, vision, sensation or movement. Because a TIA is often thought to be a prelude to full-scale stroke, patients having suffered a TIA are candidates for prophylactic stroke therapy with anticoagulation agents (e.g., coumarin and heparin) or antiplatelet agents (such as aspirin and ticlopidine), for example.

Thrombolytic agents, such as tissue plasminogen activator (t-PA), have been used in the treatment of thromboembolic stroke. These molecules function by lysing the thrombus causing the ischemia. Such drugs are believed to be most useful if administered as soon as possible after acute stroke (preferably within 3 hours) in order to at least partially restore cerebral blood flow in the ischemic region and to sustain neuronal viability. In that such drugs exacerbate bleeding, their use in hemorrhagic stroke is contra-indicated.

It has been noted that CD11a and CD18 are upregulated in leukocytes from patients who have undergone ischemic stroke or a TIA (Kim et al., J. Neurolog. Sci. 128(1):45-50 (1995)). Schroeter et al. (J. Neuroimmunology 55(2):195-203 (1994)) found that increased expression of ICAM-1 on vessels and leukocytes occurred following cerebral ischemia induced by permanent occlusion of the middle cerebral artery (MCA) in the rat.

The role of cell adhesion molecules in brain injury following transient MCA occlusion in the rat has been studied (Matsuo et al., Brain Research 656:344-352 (1994)). These researchers found that treatment with individual antibodies against cell adhesion molecules reduced edema formation, infarct size and neutrophil accumulation following reperfusion. However, to date, anti-adhesion therapy has not proved to be an effective treatment for stroke, and current established therapies for stroke are limited.

BRIEF DESCRIPTION OF THE DRAWINGS

FIG. 1 is a table showing the conivaptan treatment regimens. The five treatment groups were normal saline (control)[NS], 5% saline infusion+5% saline maintenance [5% IM], conivaptan only [C], conivaptan+5% saline maintenance [C5% M], and conivaptan+5% saline infusion+5% saline maintenance [C5% IM]. (Euth.=euthanized).

DETAILED DESCRIPTION

Figure 2:
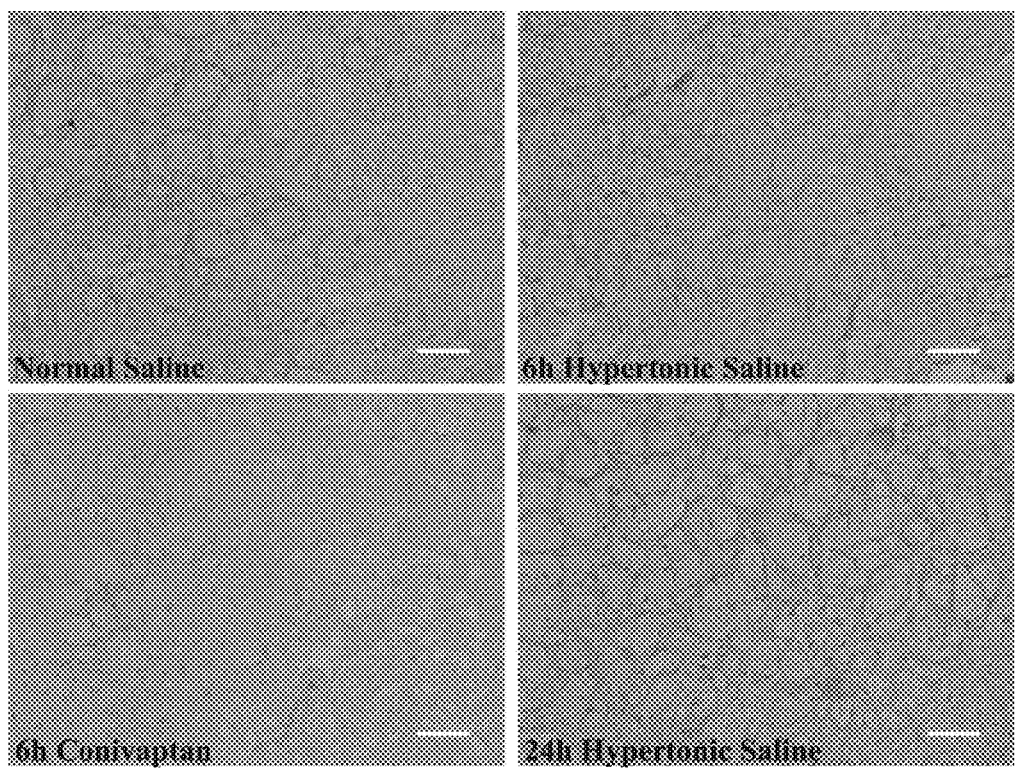
FIG. 2 is a microscopic image showing the results of CD11b staining of the infarct and surrounding areas at 48 hours post MCAO and following the various treatments as indicated.

Provided herein are methods of treating a subject believed to have suffered a stroke. These methods comprise administering to the subject a therapeutically effective amount of a composition comprising conivaptan or an active derivative, stereoisomer, pro-drug, or pharmaceutically acceptable salt thereof. Term definitions used in the specification and claims are as follows.

Definitions

As used in the specification and claims, the singular form "a," "an," and "the" include plural references unless the context clearly dictates otherwise. For example, the term "a cell" includes a plurality of cells, including mixtures thereof.

The term "active derivative" and the like means a modified conivaptan compound that retains an ability to reduce neuronal infarct size, neuronal edema and/or neuronal inflammation in a subject following a stroke.

The term "administering" refers to an administration that is oral, topical, intravenous, subcutaneous, transcutaneous, transdermal, intramuscular, intra joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques.

As used herein, unless otherwise indicated, the term "alkyl" alone or in combination refers to a monovalent saturated aliphatic hydrocarbon radical having the indicated number of carbon atoms. The radical may be a linear or branched chain and, where specified, optionally substituted with one to three suitable substituents as defined above. Illustrative examples of alkyl groups include, but are not limited to, methyl, ethyl, n-propyl, n-butyl, n-pentyl, n-hexyl, isopropyl, isobutyl, isopentyl, amyl, sec-butyl, tert-butyl, tert-pentyl, n-heptyl, n-octyl, n-nonyl, n-decyl, n-dodecyl, n-tetradecyl, n-hexadecyl, n-octadecyl, n-eicosyl and the like. Preferred alkyl groups include methyl, ethyl, n-propyl and isopropyl. Preferred optional suitable substituents include halo, methoxy, ethoxy, cyano, nitro and amino. As used herein, the term "lower alkyl" refers to a straight or branched hycrocarbon having from 1 to 10 carbon atoms.

As used herein, unless otherwise indicated, the term "alkenyl" alone or in combination refers to a monovalent aliphatic hydrocarbon radical having the indicated number of carbon atoms and at least one carbon-carbon double bond. The radical may be a linear or branched chain, in the E or Z form, and where specified, optionally substituted with one to three suitable substituents as defined above. Illustrative examples of alkenyl groups include, but are not limited to, vinyl, 1-propenyl, 2-propenyl, isopropenyl, 1-butenyl, 2-butenyl, isobutenyl, 2-methyl-1-propenyl, 1-pentenyl, 2-pentenyl, 4-methyl-2-pentenyl, 1,3-pentadienyl, 2,4-pentadienyl, 1,3-butadienyl and the like. Preferred alkenyl groups include vinyl, 1-propenyl and 2-propenyl. Preferred optional suitable substituents include halo, methoxy, ethoxy, cyano, nitro and amino.

As used herein, unless otherwise indicated, the terms "alkoxy" and "alkyloxy" alone or in combination refer to an aliphatic radical of the form alkyl-O—, wherein alkyl is as defined above. Illustrative examples of alkoxy groups include, but are not limited to, methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy, octoxy and the like. Preferred alkoxy groups include methoxy and ethoxy.

As used herein, unless otherwise indicated, the term "alkynyl" alone or in combination refers to a monovalent aliphatic hydrocarbon radical having the indicated number of carbon atoms and at least one carbon-carbon triple bond. The radical may be a linear or branched chain and, where specified, optionally substituted with one to three suitable substituents as defined above. Illustrative examples of alkynyl groups include, but are not limited to, ethynyl, 1-propynyl, 2-propynyl, 1-butynyl, 2-butynyl, 1-pentynyl, 2-pentynyl, 3-methyl-1-pentynyl, 3-pentynyl, 1-hexynyl, 2-hexynyl, 3-hexynyl and the like. Preferred alkynyl groups include ethynyl, 1-propynyl and 2-propynyl. Preferred optional suitable substituents include halo, methoxy, ethoxy, cyano, nitro and amino.

As used herein, unless otherwise indicated, the term "cycloalkyl" alone or in combination refers to a monovalent alicyclic saturated hydrocarbon radical having three or more carbons forming a carbocyclic ring and, where specified, optionally substituted with one to three suitable substituents as defined above. Illustrative examples of cycloalkyl groups include, but are not limited to, cyclopropyl, cyclobutyl, cyclopentyl, cyclohexyl, cycloheptyl, cyclooctyl, cyclononyl and the like. Preferred optional suitable substituents include halo, methyl, ethyl, methoxy, ethoxy, cyano, nitro and amino.

As used herein, unless otherwise indicated, the term "cycloalkenyl" alone or in combination refers to a monovalent alicyclic hydrocarbon radical having three or more carbons forming a carbocyclic ring and at least one carbon-carbon double bond and, where specified, optionally substituted with one to three suitable substituents as defined above. Illustrative examples of cycloalkenyl groups include, but are not limited to, cyclopentenyl, cyclohexenyl and the like. Preferred optional suitable substituents include halo, methyl, ethyl, methoxy, ethoxy, cyano, nitro and amino.

As used herein, unless otherwise indicated, the terms "alkylene," "alkenylene," "cycloalkylene" and "cycloalkenylene" refer to a divalent hydrocarbon radical that is formed by removal of a hydrogen atom from an alkyl, alkenyl, cycloalkyl or cycloalkenyl radical, respectively, as such terms are defined above.

As used herein, the term "(C3-C10 cycloalkylene)(C1-C6 alkylene)" refers to a divalent hydrocarbon radical that is formed by bonding a C3-C10 cycloalkylene radical with C1-C6 alkylene radical, as such terms are defined above.

As used herein, unless otherwise indicated, the term "aryl" alone or in combination refers to a monovalent aromatic hydrocarbon radical having six to ten carbon atoms forming a carbocyclic ring and, where specified, optionally substituted with one to three suitable substituents as defined above. Illustrative examples of aryl groups include, but are not limited to, phenyl, naphthyl, tetrahydronaphthyl, indanyl and the like. Preferred aryl groups are phenyl and naphthyl, optionally mono- or disubstituted by identical or different suitable substituents selected from halo, cyano, C1-C3 alkyl, C3-C6 cycloalkyl, difluoromethyl, trifluoromethyl, C1-C3 alkoxy, difluoromethoxy and trifluoromethoxy.

As used herein, unless otherwise indicated, the term "heterocycloalkyl" alone or in combination refers to a cycloalkyl group as defined above in which one or more carbons in the ring is replaced by a heteroatom selected from N, S and O. Illustrative examples of heterocycloalkyl groups include, but are not limited to, pyrrolidinyl, tetrahydrofuranyl, piperazinyl, tetrahydropyranyl, and the like.

As used herein, unless otherwise indicated, the term "heteroaryl" alone or in combination refers to a monovalent aromatic heterocyclic radical having two to nine carbons and one to four heteroatoms selected from N, S and O forming a five- to ten-membered monocyclic or fused bicyclic ring and, where specified, optionally substituted with one to three suitable substituents as defined above. Illustrative examples of heteroaryl groups include, but are not limited to, pyridyl, pyridazinyl, pyrazinyl, pyrimidinyl, triazinyl, quinolinyl, isoquinolinyl, quinoxalinyl, quinazolinyl, benzotriazinyl, benzimidazolyl, benzopyrazolyl, benzotriazolyl, benzisoxazolyl, isobenzofuryl, isoindolyl, indolizinyl, thienopyridinyl, thienopyrimidinyl, pyrazolopyrimidinyl, imidazopyridines, benzothiaxolyl, benzofuranyl, benzothienyl, indolyl, isothiazolyl, pyrazolyl, indazolyl, imidazolyl, triazolyl, tetrazolyl, oxazolyl, isoxazolyl, oxadiazolyl, thiadiazolyl, pyrrolyl, thiazolyl, furyl, thienyl and the like. Five- or six-membered monocyclic heteroaryl rings include pyridyl, pyridazinyl, pyrazinyl, pyrimidinyl, triazinyl, isothiazolyl, pyrazolyl, imidazolyl, triazolyl, tetrazolyl, oxazolyl, isoxazolyl, oxadiazolyl, thiadiazolyl, pyrrolyl, thiazolyl, furyl, thienyl and the like. Eight- to ten-membered bicyclic heteroaryl rings having one to four heteroatoms include: quinolinyl, isoquinolinyl, quinoxalinyl, quinazolinyl, benzotriazinyl, benzimidazolyl, benzopyrazolyl, benzotriazolyl, benzisoxazolyl, isobenzofuryl, isoindolyl, indolizinyl, thienopyridinyl, thienopyrimidinyl, pyrazolopyrimidinyl, imidazopyridinyl, benzothiaxolyl, benzofuranyl, benzothienyl, indolyl, indazolyl, and the like. Preferred optional suitable substitutions include one or two identical or different substituents selected from halo, cyano, C1-C3 alkyl, C3-C6 cycloalkyl, difluoromethyl, trifluoromethyl, C1-C3 alkoxy, difluoromethoxy and trifluoromethoxy.

As used herein, unless otherwise indicated, the term "haloalkyl" refers to an alkyl radical as described above substituted with one or more halogens. Illustrative examples of haloalkyl groups include, but are not limited to, chloromethyl, dichloromethyl, fluoromethyl, difluoromethyl, trifluoromethyl, 2,2,2-trichloroethyl and the like.

As used herein, unless otherwise indicated, the term "haloalkoxy" refers to an alkoxy radical as described above substituted with one or more halogens. Illustrative examples of haloalkoxy groups include, but are not limited to, trifluoromethoxy, difluoromethoxy and the like.

As used herein, unless otherwise indicated, the term "aralkyl" refers to an alkyl radical of one to six carbons as described above substituted with an aryl group as described above.

As used herein, unless otherwise indicated, the term "heteroaralkyl" refers to an alkyl radical of one to six carbons as described above substituted with a heteroaryl group as described above.

As used herein, unless otherwise indicated, the term "aralkoxy" refers to an alkoxy radical of one to six carbons as described above substituted with an aryl group as described above.

As used herein, unless otherwise indicated, the term "heteroaralkoxy" refers to an alkoxy radical of one to six carbons as described above substituted with a heteroaryl group as described above.

As used herein, unless otherwise indicated, the term "carbamoyl" refers to a monovalent radical of the form —C(O)NH(R), wherein R is hydrogen, C1-C6 alkyl, C2-C6 alkenyl, C3-C6 cycloalkyl, or aryl as such terms are defined above.

As used herein, unless otherwise indicated, the terms "di-(C1-C3 alkyl)amino" and "di-(C1-C6 alkyl)amino" alone or in combination refer to an amino group that is substituted with two groups independently selected from C1-C3 alkyl or C1-C6 alkyl, respectively.

As used herein, the term "comprising" is intended to mean that the compositions and methods include the recited elements, but not excluding others. "Consisting essentially of," when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this disclosure.

A "control" is an alternative subject or sample used in an experiment for comparison purpose. A control can be "positive" or "negative."

An "effective amount" is an amount sufficient to effect beneficial or desired results. An effective amount can be administered in one or more administrations, applications or dosages.

As used herein, the term "halo" means a monovalent halogen radical or atom selected from fluoro, chloro, bromo and iodo. Preferred halo groups are fluoro, chloro and bromo.

"Mammal" for purposes of treatment refers to any animal classified as a mammal, including human, domestic and farm animals, nonhuman primates, and zoo, sports, or pet animals, such as dogs, horses, cats, cows, etc.

A "pharmaceutical composition" is intended to include the combination of an active agent with a carrier, inert or active, making the composition suitable for diagnostic or therapeutic use in vitro, in vivo or ex vivo.

The term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives.

The term "pharmaceutically acceptable" means a material that is not biologically or otherwise undesirable, i.e., the material can be administered to an individual along with the selected compound without causing any undesirable biological effects or interacting in a deleterious manner with any of the other components of the pharmaceutical composition in which it is contained.

The term "pharmaceutically acceptable salt(s)," unless otherwise indicated, includes salts of acidic or basic groups that may be present in the compounds of Formula I.

The terms "pharmaceutically effective amount," "therapeutically effective amount" or "therapeutically effective dose" refer to the amount of a compound such as conivaptan or an active derivative of conivaptan that will elicit the biological or medical response of a tissue, system, animal, or human that is being sought by the researcher, veterinarian, medical doctor or other clinician. In some embodiments, the biological response is a reduction in neural infarct size, edema and/or inflammation following a stroke as compared to a control. The term "therapeutically effective amount" includes that amount of a compound such as conivaptan or an active derivative, stereoisomer, pro-drug, or pharmaceutically acceptable salt thereof, that, when administered, is sufficient to prevent development of, or alleviate to some extent, one or more of the symptoms of the condition or disorder being treated. The therapeutically effective amount will vary depending on the compound such as a conivaptan or an active derivative, stereoisomer, pro-drug, or pharmaceutically acceptable salt thereof, the disorder or conditions and its severity, the route of administration, time of administration, rate of excretion, drug combination, judgment of the treating physician, dosage form, and the age, weight, general health, sex and/or diet of the subject to be treated.

In the context of the present method, a pharmaceutically or therapeutically effective amount or dose of a conivaptan or an active derivative, stereoisomer, pro-drug, or pharmaceutically acceptable salt thereof, includes an amount that is sufficient to prevent development of, or reduce, neural edema, neural inflammation, neural damage, or combinations thereof. In some embodiments, the neural infarct size is reduced upon administration of a pharmaceutically or therapeutically effective amount or dose of a conivaptan or an active derivative, stereoisomer, pro-drug, or pharmaceutically acceptable salt thereof.

The terms "prevent," "preventing," "prevention" and grammatical variations thereof as used herein, refer to a method of partially or completely delaying or precluding the onset or recurrence of a disorder or conditions and/or one or more of its attendant symptoms or barring a subject from acquiring or reacquiring a disorder or condition or reducing a subject's risk of acquiring or reacquiring a disorder or condition or one or more of its attendant symptoms.

The term "stroke" is used herein to refer to a rapid loss of brain function due to a disturbance in the blood supply to the brain. Disturbance in the blood supply can be caused by blockage, hemorrhage, or other condition. As used herein, a "stroke effect" includes, but is not limited to, a neural infarct, neural edema, neural inflammation, vision disturbances, seizures, incontinence, paralysis, pain, fatigue, vascular dementia, aphasis, short-term memory loss, long-term memory loss, depression, and pseudobulbar affect.

The terms "subject," "individual" and "patient" are used interchangeably herein, and refer to a vertebrate, preferably a mammal, more preferably a human. Mammals include, but are not limited to, murines, simians, humans, farm animals, sport animals, and pets.

As used herein, the term "suitable substituent" means a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents may be selected from the group consisting of halo, C1-C6 alkyl, C2-C6 alkenyl, C1-C6 haloalkyl, C1-C6 alkoxy, C1-C6 haloalkoxy, C2-C6 alkynyl, C3-C8 cycloalkenyl, (C3-C8 cycloalkyl)C1-C6 alkyl, (C3-C8 cycloalkyl)C2-C6 alkenyl, (C3-C8 cycloalkyl)C1-C6 alkoxy, C3-C7 heterocycloalkyl, (C3-C7 heterocycloalkyl)C1-C6 alkyl, (C3-C7 heterocycloalkyl)C2-C6 alkenyl, (C3-C7 heterocycloalkyl)C1-C6 alkoxy, hydroxy, carboxy, oxo, sulfanyl, C1-C6 alkylsulfanyl, aryl, heteroaryl, aryloxy, heteroaryloxy, aralkyl, heteroaralkyl, aralkoxy, heteroaralkoxy, nitro, cyano, amino, C1-C6 alkylamino, di-(C1-C6 alkyl)amino, carbamoyl, (C1-C6 alkyl) carbonyl, (C1-C6 alkoxy)carbonyl, (C1-C6 alkyl)aminocarbonyl, di-(C1-C6 alkyl)aminocarbonyl, arylcarbonyl, aryloxycarbonyl, (C1-C6 alkyl)sulfonyl, and aryl sulfonyl. The groups listed above as suitable substituents are as defined hereinafter except that a suitable substituent may not be further optionally substituted.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more (e.g., referred to as "disubstitued," "trisubstituted," and the like) and the same or different for appropriate organic compounds. For purposes of this disclosure, the heteroatoms, such as nitrogen and oxygen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. Also, as used herein "substitution" or "substituted with" is meant to encompass configurations where one substituent is fused to another substituent. For example, an aryl group substituted with an aryl group (or vice versa) can mean that one aryl group is bonded to the second aryl group via a single sigma bond and also that the two aryl groups are fused, e.g., two carbons of one alkyl group are shared with two carbons of the other aryl group.

The terms "treat," "treating," "treatment" and grammatical variations thereof as used herein include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, pallatively or remedially. In some instances, the terms "treat," "treating," "treatment" and grammatical variations thereof include reducing one or more of: the size of a neural infarct, neural edema, neural inflammation, vision disturbances, seizures, incontinence, paralysis, pain, fatigue, vascular dementia, aphasis, short-term memory loss, long-term memory loss, depression, and pseudobulbar affect as compared with prior to treatment of the subject or as compared with the incidence of such symptom in a general or stroke study population.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixtures.

Description

Provided herein is a method of treating a subject believed to have suffered a stroke. These methods comprise administering to the subject a therapeutically effective amount of a composition comprising conivaptan, or an active derivative, stereoisomer, pro-drug, or pharmaceutically acceptable salt thereof. Conivaptan and some of its active derivatives, stereoisomers, pro-drugs, and/or pharmaceutically acceptable salts, are disclosed in U.S. Pat. Nos. 6,740,648 and 7,192,951, which are hereby incorporated by reference in their entirety. In some embodiments, the conivaptan active derivative has the following chemical formula (Formula I):

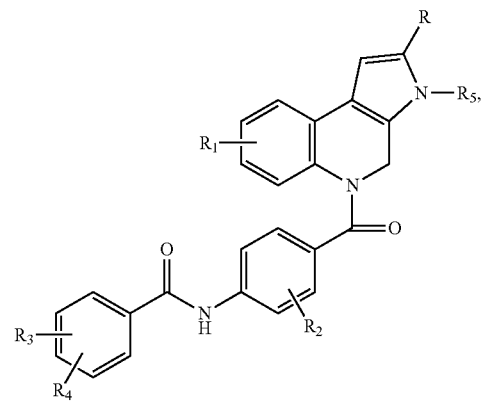

wherein R and $R_5$ are hydrogen or a lower alkyl; $R_1$, $R_2$ and $R_3$ independently are hydrogen, halogen, lower alkyl, lower alkoxy, amino, alkylamino, or dialkylamino; and $R_4$ is hydrogen, phenyl or substituted phenyl, and pharmaceutically acceptable salts thereof.

In one embodiment, conivaptan has the following chemical formula (Formula II):

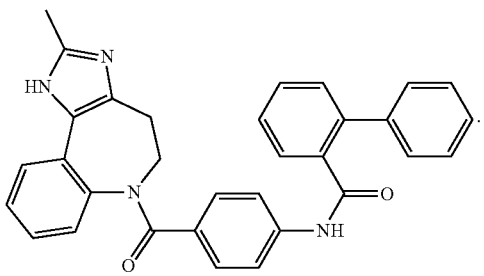

Described herein is the surprising finding that conivaptan can be effectively administered after the first 1, 2, 3, 4, 5 or 6 hours following a stroke. "Effectively administered" indicates that such administration results in the treatment of a stroke effect. For example, administration of conivaptan or an active derivative, stereoisomer, pro-drug, or pharmaceutically acceptable salt thereof, more than 1, 2, 3, 4, 5 or 6 hours after a stroke results in a decrease in neural infarct size, a decrease in neural edema, and/or a decrease in neural inflammation, and/or a reduction in one or more of: vision disturbances, seizures, incontinence, paralysis, pain, fatigue, vascular dementia, aphasis, short-term memory loss, long-term memory loss, depression, and pseudobulbar affect as compared to a control subject.

In some embodiments, the composition is first administered to a subject believed to have suffered a stroke up to approximately 12 hours after the stroke. For example, a therapeutically effective amount of a composition comprising conivaptan, or an active derivative, stereoisomer, pro-drug, or pharmaceutically acceptable salt thereof, can be first administered within approximately the first 1, 2, 3, 4, 5, 6, 7, 8, 9, 10, 11 or 12 hours after the stroke (or the estimated time of the stroke). In some embodiments, the conivaptan, or an active derivative, stereoisomer, pro-drug, or pharmaceutically acceptable salt thereof, is administered to the subject between approximately 3 and 12 hours, 3 and 9 hours, 3 and 8 hours, 3 and 7 hours, or 3 and 6 hours after the subject's stroke. In other embodiments, the conivaptan, or an active derivative, stereoisomer, pro-drug, or pharmaceutically acceptable salt thereof, is administered to the subject between approximately 4 and 12 hours, 4 and 9 hours, 4 and 8 hours, 4 and 7 hours, or 4 and 6 hours after the subject's stroke. In still other embodiments, the conivaptan, or an active derivative, stereoisomer, pro-drug, or pharmaceutically acceptable salt thereof, is administered to the subject between approximately 5 and 12 hours, 5 and 9 hours, 5 and 8 hours, or 5 and 7 hours after the subject's stroke. In still other embodiments, the conivaptan, or an active derivative, stereoisomer, pro-drug, or pharmaceutically acceptable salt thereof, is administered to the subject between approximately 6 and 12 hours, 6 and 9 hours, 6 and 8 hours, or 6 and 7 hours after the subject's stroke. In one embodiment, the conivaptan, or an active derivative, stereoisomer, pro-drug, or pharmaceutically acceptable salt thereof, is administered to the subject approximately 6 hours after the subject's stroke.

In some embodiments, a therapeutically effective amount of a first dose of conivaptan, or an active derivative, stereoisomer, pro-drug, or pharmaceutically acceptable salt thereof, is between approximately 0.20 and 0.50 mg/kg or 0.30 and 0.40 mg/kg. In one embodiment, a therapeutically effective amount of a first dose of conivaptan, or an active derivative, stereoisomer, pro-drug, or pharmaceutically acceptable salt thereof, is approximately 0.35 mg/kg.

Following the first administration, the conivaptan, or an active derivative, stereoisomer, pro-drug, or pharmaceutically acceptable salt thereof, can be administered to the subject continuously or intermittently for up to approximately 72, 48, 24, or 12 hours after the stroke. In some embodiments, the one or more subsequent administrations are at a dosage of approximately four to five times less than the first administration dosage. Accordingly, the one or more subsequent administrations can be at a dosage of between approximately 0.04 and 0.125 mg/kg or 0.06 and 0.10 mg/kg. In one embodiment, a therapeutically effective amount of a second or subsequent dose of conivaptan, or an active derivative, stereoisomer, pro-drug, or pharmaceutically acceptable salt thereof, is approximately 0.07 mg/kg.

It should be understood that a conivaptan, or an active derivative, stereoisomer, pro-drug, or pharmaceutically acceptable salt thereof, can be administered in a treatment regimen that includes one or more additional stroke treatment compounds. For example, a conivaptan, or an active derivative, stereoisomer, pro-drug, or pharmaceutically acceptable salt thereof, can be administered with a blood clot degradation compound, including, but not limited to, a tissue plasminogen activator.

Accordingly, included herein are pharmaceutical compositions comprising conivaptan, or an active derivative, stereoisomer, pro-drug, or pharmaceutically acceptable salt thereof. The pharmaceutical compositions containing the active ingredient can be in a form suitable for oral use, for example, as tablets, troches, lozenges, aqueous or oily suspensions, dispersible powders or granules, emulsions, hard or soft capsules, syrups, or elixirs. Dosage levels of the order of 0.04 mg to 10 mg per kilogram of body weight per day are useful in the treatment of the above-indicated conditions. The amount of active ingredient that may be combined with carrier materials to produce a single dosage form will vary depending upon the host treated and the particular mode of administration.

For injection, the therapeutic amount of the conivaptan or its pharmaceutically acceptable salts, derivatives or prodrugs will normally be in the dosage range from 0.04 mg to 10 mg/kg of body weight. Administration is made by intravenous, intramuscular, or subcutaneous injection. In addition to the active ingredient, these pharmaceutical compositions will usually contain a buffer, e.g. a phosphate buffer which keeps the pH in the range from 3.5 to 7 and sodium chloride, mannitol, or sorbitol for adjusting the isotonic pressure.

A composition for topical application can be formulated as an aqueous solution, lotion, jelly or an oily solution or suspension, ointments, creams, gels, drops, suppositories, sprays, liquids and powders. Conventional pharmaceutical carriers, aqueous, powder or oily bases, thickeners and the like can be desirable. A composition in the form of an aqueous solution is obtained by dissolving the compounds disclosed herein in aqueous buffer solution of pH 4 to 6.5 and, if desired, adding a polymeric binder. An oily formulation for topical application is obtained by suspending the compounds disclosed herein in an oil, optionally with the addition of a swelling agent such as aluminum stearate and/or a surfactant.

Preparations for parenteral administration include sterile aqueous or non-aqueous solutions, suspensions, and emulsions. Examples of non-aqueous solvents are propylene glycol, polyethylene glycol, vegetable oils such as olive oil, marine oils, and injectable organic esters such as ethyl oleate. Aqueous carriers include water, alcoholic/aqueous solutions, and emulsions or suspensions, including saline and buffered media. Parenteral vehicles include sodium chloride solution, Ringer's dextrose, dextrose and sodium chloride, lactated Ringer's, and fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Some of the formulations can potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

It should be understood that the foregoing relates to preferred embodiments of the present disclosure and that numerous changes may be made therein without departing from the scope of the disclosure. The disclosure is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present disclosure and/or the scope of the appended claims. All patents, patent applications, and publications referenced herein are incorporated by reference in their entirety for all purposes.

EXAMPLES

Example 1

Permanent middle cerebral artery occlusion (MCAO) was induced in rats. Post MCAO, conivaptan was administered to the rat via jugular catheter at varying times and dosages. The conivaptan used was VAPRISOL® which is a conivaptan hydrochloride premixed in 5% dextrose at 20 mg/100 ml in 100 ml IV bag. The conivaptan was purchased from Astellas Pharma USA, Inc. (lot#0789065) and sub-aliquoted into sterile foil-covered vials.

For rats receiving the 6-hour treatment, 0.5 ml (0.35 mg/kg) bolus conivaptan was administered six hours post MCAO, followed by administrations of 0.1 ml (0.07 mg/kg) conivaptan at nine hours post MCAO. At 20, 24, 28, and 32 hours post MCAO, 0.1 ml (0.07 mg/kg) conivaptan was administered. A saline control (1.4 ml of 0.9% saline) was then injected at 44 hours post MCAO. At 48 hours post MCAO, the rats were euthanized.

For rats receiving the 24-hour treatment, 0.5 ml (0.35 mg/kg) bolus conivaptan was administered 24 hours post MCAO, followed by administrations of 0.1 ml (0.07 mg/kg) conivaptan at 20, 24, 28 and 32 hours post MCAO. Saline controls (1.4 ml of 0.9% saline) were injected at 6, 9, and 44 hours post MCAO. At 48 hours post MCAO, the rats were euthanized.

The mortality rate prior to euthanization is provided below in Table 1:

TABLE 1

| Sample | FD | Data (total) | % Survival (total) | ED Catheter | Omitted |
|---|---|---|---|---|---|
| Control | 12 | 13 (18) | 52 (60) | 2 | 5 |
| 6 hour | 2 | 7 (9) | 78 (82) | 1 | 2 |
| 24 hour | 4 | 5 | 56 | 1 | 0 |

Fluoro-Jade staining of neural biopsies obtained from the site of the infarct was also performed and the results are shown in Table 2.

TABLE 2

| Sample | Avg (g) | Std Dev | Std Error |
|---|---|---|---|
| Control (n = 13) | 59.988 | 26.125 | 7.246 |
| 6 hour (n = 7) | 38.331 | 30.127 | 11.38* |
| 24 hour (n = 5) | 55.388 | 29.554 | 13.217** |

*p = .06 compared to controls 37% decrease
**p = 0.3 compared to controls

Example 2

Permanent middle cerebral artery occlusion (MCAO) was induced in rats. Post MCAO, conivaptan, hyper saline or normal saline was administered to the rats via jugular catheter at varying times and dosages. The conivaptan used was Vaprisol® which is a conivaptan hydrochloride premixed in 5% dextrose at 20 mg/100 ml in 100 ml IV bag. The conivaptan was purchased from Astellas Pharma USA, Inc. (lot#0789065) and sub-aliquoted into sterile foil-covered vials. Hyper saline solutions were 5% NaCl. Saline solutions were 0.9% NaCl.

Figure 3:
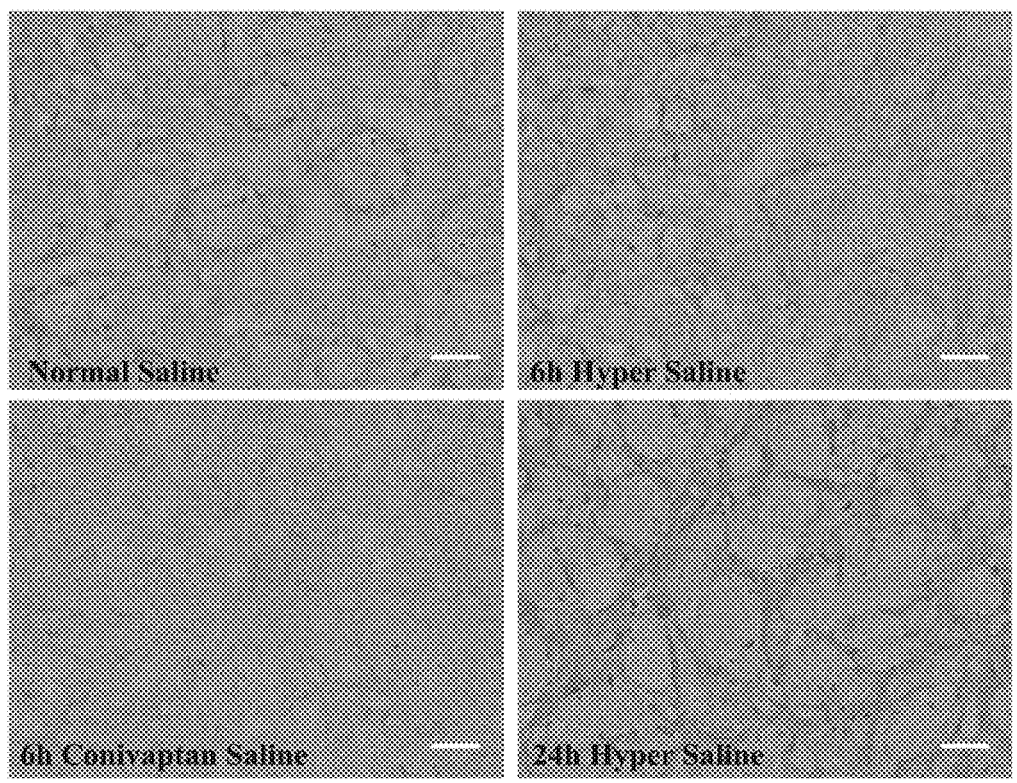
FIG. 3 is a is a microscopic image showing the results of CD11b staining of the infarct and surrounding areas at 48 hours post MCAO and following the various treatments as indicated.
Figure 4:
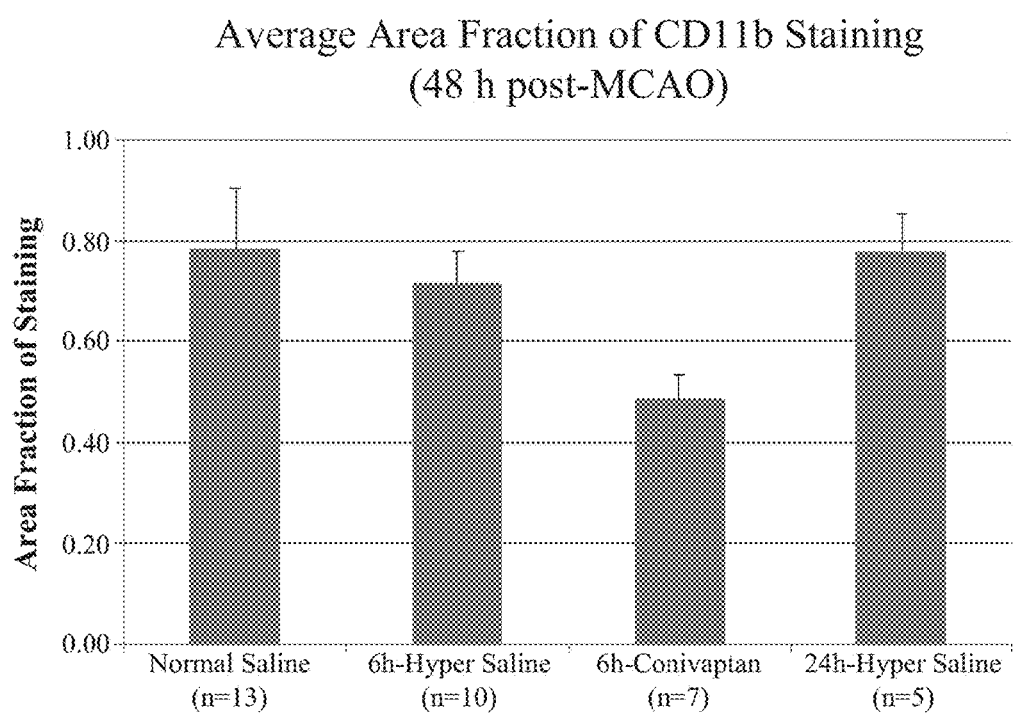
FIG. 4 is a graph showing the average area fraction of CD11b staining at 48 hours post MCAO following the various treatments.

For rats receiving the six-hour treatment, 0.5 ml (0.35 mg/kg) bolus conivaptan was administered 6 hours post MCAO, followed by administrations of 0.1 ml (0.07 mg/kg) conivaptan at 9 hours post MCAO. At 20, 24, 28, and 32 hours post MCAO, 0.1 ml (0.07 mg/kg) conivaptan was administered. A saline control (1.4 ml of 0.9% saline) was then injected at 44 hours post MCAO. At 48 hours post MCAO, the rats were euthanized. The treatment regimen is provided in FIG. 1 and the results of such treatment are shown in Table 3 below. FIGS. 2, 3 and 4 further show the results of CD11b staining of the infarct and surrounding areas at 48 hours post MCAO and following the various treatments as indicated.

TABLE 3

| Sample | Avg | St Dev | St Error |
|---|---|---|---|
| Normal Saline (n = 13) | 0.785 | 0.428 | 0.12 |
| 6 h-Hyper Saline (n = 10) | 0.716 | 0.203 | 0.06 |
| 6 h-Conivaptan (n = 7) | 0.486 | 0.125 | 0.05 |
| 24 h-Hyper Saline (n = 5) | 0.778 | 0.170 | 0.08 |
| t-test: 1-tailed, unequal variance | p = | | |
| Normal vs 6 h Hyper Saline | 0.3091 | | |

TABLE 3-continued

| Sample | Avg | St Dev | St Error |
| --- | --- | --- | --- |
| Normal vs 6 h Conivaptan | 0.0167 | | |
| Normal vs 24 h Hyper Saline | 0.4821 | | |
| 6 h Conivaptan vs 6 h Hyper Saline | 0.0057 | | |
| 6 h Conivaptan vs 24 h Hyper Saline | 0.0068 | | |

The invention claimed is:

1. A method of treating a stroke or a suspected stroke in a subject in need thereof comprising:
administering a first pharmaceutical formulation comprising a first amount of conivaptan or a pharmaceutically acceptable salt thereof to the subject in need thereof within 6 hours of stroke or estimated time of stroke, wherein the first amount is 0.35 mg/kg of bodyweight; and
administering a second pharmaceutical formulation comprising a second amount of conivaptan or a pharmaceutically acceptable salt thereof to the subject in need thereof within 9 hours, 20 hours, 24 hours, 28 hours and 32 hours of stroke or estimated time of stroke, wherein the second amount is 0.07 mg/kg of bodyweight, wherein the administration of the first pharmaceutical formulation and the second pharmaceutical formulation is effective to reduce brain infarct size in the subject in need thereof.

2. The method of claim 1, wherein the subject has not received an amount of conivaptan or the pharmaceutically acceptable salt thereof prior to the stroke or suspected stroke.

3. The method of claim 1, wherein the first amount, the second amount, or the first amount and the second amount is administered via intravenous injection.

4. The method of claim 1, wherein the first pharmaceutical formulation comprises a pharmaceutically acceptable salt of conivaptan.

5. The method of claim 1, wherein the first pharmaceutical formulation comprises conivaptan hydrochloride.

6. The method of claim 1, wherein the second pharmaceutical formulation comprises a pharmaceutically acceptable salt of conivaptan.

7. The method of claim 6, wherein the second pharmaceutical formulation comprises conivaptan hydrochloride.

8. The method of claim 7, wherein the first pharmaceutical formulation comprises a pharmaceutically acceptable salt of conivaptan.

9. The method of claim 7, wherein the first pharmaceutical formulation comprises conivaptan hydrochloride.

10. The method of claim 6, wherein the first pharmaceutical formulation comprises a pharmaceutically acceptable salt of conivaptan.

11. The method of claim 6, wherein the first pharmaceutical formulation comprises conivaptan hydrochloride.

12. The method of claim 1, further comprising the step of administering an amount of a plasminogen activation compound to the subject in need thereof.

13. The method of claim 12, wherein the plasminogen activation compound is tissue plasminogen activator.

* * * * *